(12) United States Patent
Chen et al.

(10) Patent No.: US 9,649,323 B2
(45) Date of Patent: May 16, 2017

(54) METHODS OF USING DUAL-EFFECT LIPOSOME IN THERAPY

(75) Inventors: Chin-Tin Chen, Taipei (TW); Tsuimin Tsai, Taipei (TW)

(73) Assignees: NATIONAL TAIWAN UNIVERSITY, Taipei (TW); TAIPEI MEDICAL UNIVERSITY, Taipei (TW)

( * ) Notice: Subject to any disclaimer, the term of this patent is extended or adjusted under 35 U.S.C. 154(b) by 982 days.

(21) Appl. No.: 13/474,998

(22) Filed: May 18, 2012

(65) Prior Publication Data

US 2012/0323163 A1 Dec. 20, 2012

Related U.S. Application Data

(60) Provisional application No. 61/487,453, filed on May 18, 2011.

(51) Int. Cl.

| A61K 9/127 | (2006.01) |
|---|---|
| A61K 31/704 | (2006.01) |
| A61K 33/24 | (2006.01) |
| A61K 41/00 | (2006.01) |
| A61K 9/00 | (2006.01) |

(52) U.S. Cl.
CPC .......... *A61K 31/704* (2013.01); *A61K 9/0019* (2013.01); *A61K 9/1271* (2013.01); *A61K 33/24* (2013.01); *A61K 41/0071* (2013.01)

(58) Field of Classification Search
CPC ...................................... A61K 9/127
USPC .......................................... 424/450
See application file for complete search history.

(56) References Cited

U.S. PATENT DOCUMENTS

| 5,277,913 A * | 1/1994 | Thompson et al. .......... 424/450 |
| 2005/0130952 A1* | 6/2005 | Levy et al. .................. 514/185 |
| 2009/0156552 A1* | 6/2009 | Cooper et al. ................ 514/63 |
| 2010/0034749 A1* | 2/2010 | Schulze et al. ............... 424/9.6 |

FOREIGN PATENT DOCUMENTS

WO 2004/058352 * 7/2004

* cited by examiner

*Primary Examiner* — Gollamudi Kishore
(74) *Attorney, Agent, or Firm* — WPAT, P.C.; Anthony King

(57) ABSTRACT

The invention provides a method for treating target in need of such a treatments in a subject, comprising (a) administering a liposome containing a photosensitizer and a drug to a subject and (b) irradiating targets at least one time at appropriate time(s). In particular, the irradiation is performed at least two times.

6 Claims, 18 Drawing Sheets

(A)

(B)

METHODS OF USING DUAL-EFFECT LIPOSOME IN THERAPY

CROSS-REFERENCE TO RELATED APPLICATIONS

This application claims priority to U.S. Provisional Pat. Application No. 61/487,453, filed on May 18, 2011 and is hereby incorporated by reference in its entirety.

Although incorporated by reference in its entirety, no arguments or disclaimers made in the provisional application apply to this divisional application. Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

FIELD OF THE INVENTION

The invention provides a method for treating target in need of such a treatments in a subject, comprising (a) administering a liposome containing a photosensitizer and a drug to a subject and (b) irradiating the targets at least one time at appropriate time(s). In particular, the irradiation is performed at least two times.

BACKGROUND OF THE INVENTION

Liposomes are artificial vesicles composed of concentric lipid bilayers separated by water-compartments and have been extensively investigated as drug delivery vehicles. Due to their structure, chemical composition and colloidal size, all of which can be well controlled by preparation methods, liposomes exhibit several properties which may be useful in various applications. The most important properties are colloidal size, i.e. rather uniform particle size distributions in the range of 20 nm to 10 µm, and special membrane and surface characteristics. Liposomes are used as carriers for drugs and antigens because they can serve several different purposes. Liposome encapsulated drugs are inaccessible to metabolizing enzymes. Conversely, body components (such as erythrocytes or tissues at the injection site) are not directly exposed to the full dose of the drug. The duration of drug action can be prolonged by liposomes because of a slower release of the drug in the body. Liposomes have a direction potential, which means that targeting options change the distribution of the drug in the body. Cells use endocytosis or phagocytosis mechanism to take up liposomes into the cytosol. Furthermore, liposomes can protect a drug against degradation (e.g. metabolic degradation). However, liposomes may confront a defect that drugs (such as anti-cancer drugs) encapsulated in liposomes cannot be well released.

Photodynamic therapy ("PDT") is a process whereby light of a specific wavelength is directed to tissues undergoing treatment or investigation that have been rendered photosensitive through the administration of a photoreactive or photosensitizing agent. Initiation of photodynamic activity is caused by excitation of the photodynamic compound by light that falls within its absorption band. The wavelength specificity depends on the molecular structure of the photodynamic compound; a greater degree of conjugation within a molecule leads to greater absorbance at longer wavelengths. Activation of photodynamic compounds occurs with subablative light fluences. Toxicity is achieved by $O_2$ radical toxicity. The singlet $O_2$ reacts with, for example, double bonds to produce reactive species, for example, organoperoxides. These, in turn, initiate free radical chain reactions which degrade and disorganize membranes, uncouple oxidative phosphorylation, and lead to cellular disruption. However, PDT is only suitable for superficial therapy.

Photodynamic therapy (PDT) is being used experimentally to treat a wide variety of malignant tumors and certain other diseases, such as psoriasis and papillomatosis. This technology is disclosed in U.S. Pat. Nos. 4,649,151, 4,866,168, 4,889,129 and 4,932,934, the disclosure of which is incorporated herein by reference. Photodynamic therapy has proven to be very effective in destroying abnormal tissue such as cancer cells. In this therapy, a photoreactive agent having a characteristic light absorption wavelength or waveband is first administered to the patient. Abnormal tissue in the body is known to selectively absorb certain photoreactive agents to a much greater extent than normal tissue, e.g., tumors of the pancreas and colon may absorb two to three times the volume of these agents, compared to normal tissue. Certain porphyrins and related tetrapyrrolic compounds tend to localize in abnormal tissue, including malignant tumors and other hyperproliferative tissue, such as hyperproliferative blood vessels, in much higher concentrations than in normal tissues, so they are useful as a tool for the treatment of various type of cancers and other hyperproliferative tissue by photodynamic therapy (PDT). However, most of the porphyrin-based photosensitizers including PHOTOFRIN™ (a purified hematoporphyrin derivative (HpD) approved worldwide for the treatment of tumors) clear slowly from normal tissue, so patients must avoid exposure to sunlight for a significant time after treatment.

U.S. Pat. Nos. 5,705,518 and 5,770,619 of Richer et al. describe a PDT experiment where a photosensitizer, benzoporphyrin derivative mono-acid ring A (BPD-MA) was prepared as its liposome and intravenously administered to a mouse having transplanted M-1 tumor, followed by irradiating the mouse with an exciting laser beam. Based on these experiments, a method is proposed for destroying or impairing an area of neovascularization, which comprises transcutaneously irradiating said area with a laser light before an administered photosensitizer has permeated into dermal tissue or other normal tissues, so that the dermal phototoxicity can be avoided. In U.S. Pat. Nos. 5,705,518 and 5,770,619, Richter et al. refer to mono-L-aspartyl chlorin e6 as one example of the photosensitizer, and indicate that the method as proposed could be used to destroyed or impair an area of neovascularization formed in the eye.

U.S. Pat. No. 5,277,913 provides a triggered release liposomal delivery system that selectively releases its contents in response to illumination or reduction in pH. The liposomes contain an amphipathic lipid, such as a phospholipid, having two chains derived from fatty acid that allow the lipid to pack into a bilayer structure. One or both of the alkyl chains contain a vinyl ether functionality that is cleaved by reactive oxygen species (ROS) or acid. A photosensitizer is incorporated into the liposomal cavity or membrane, and produces ROS or acid when illuminated to cleave the vinyl ether functionality and disrupt the liposomal membrane to release the vesicle contents.

The use of PDT for the treatment of various types of disease has been limited due to the inherent features of photosensitizers (PS). These include high cost, extended retention in the host organism, substantial skin photo toxicity, low solubility in physiological solutions (which also reduces its usefulness for intravascular administration as it can provoke thromboembolic accidents), and low targeting effectiveness. These disadvantages, particularly of PS in the prior art, has led to the administration of very high doses of a photosensitizer, which dramatically increase the possibility of accumulation of the photosensitizer in non-damaged tissues and the accompanying risk of affecting non-damaged sites.

Since the application of photodynamic therapy in the treatment of cancer and other diseases is increasing rapidly, there is also a greater demand for a new PDT regimen.

SUMMARY OF THE INVENTION

The invention provides a method for photodynamic therapy in target tissues in a subject, comprising (a) administering a therapeutically effective dose of liposome containing a photosensitizer and a drug to a subject and (b) irradiating the target tissues at least one time at appropriate time(s). Also provided is a use of a liposome containing a photosensitizer and a drug in the manufacture of a medicament for photodynamic therapy in target tissues in a subject, wherein a therapeutically effective dose of the liposome containing a photosensitizer and a drug is administered to a subject and a irradiation is applied onto the target tissues at least one time at appropriate time(s).

The invention also provides a method for photodynamic therapy in a subject, comprising (a) administering a therapeutically effective dose of liposome containing a photosensitizer and a drug to a subject, (b) performing a first irradiation to the tumor tissues at the time the drug reaches the tumors, (c) performing a second irradiation to the tumor tissues at the time the drug accumulates at the target tissues to a maximum amount, and optionally (d) performing other irradiations to the target tissues. Also provided is a use of a liposome containing a photosensitizer and a drug in the manufacture of a medicament for photodynamic therapy in target tissues in a subject, wherein a therapeutically effective dose of liposome containing a photosensitizer and a drug is administered to a subject, a first irradiation is applied onto the tumor tissues at the time the drug reaches the tumors and a second irradiation is applied onto the tumor tissues at the time the drug accumulates at the target tissues to a maximum amount, and optionally other irradiations are applied onto the target tissues.

The invention also provides a liposome composition, comprising liposome, a photosensitizer Ce6 or Npe6 and an anti-cancer drug, wherein the photosensitizer and the anti-cancer drug are encapsulated within the liposome and the ratios of the liposome and photosensitizer are 60-90% to 0.2-0.80% (w/w), respectively.

DETAILED DESCRIPTION OF THE INVENTION

Figure 1:
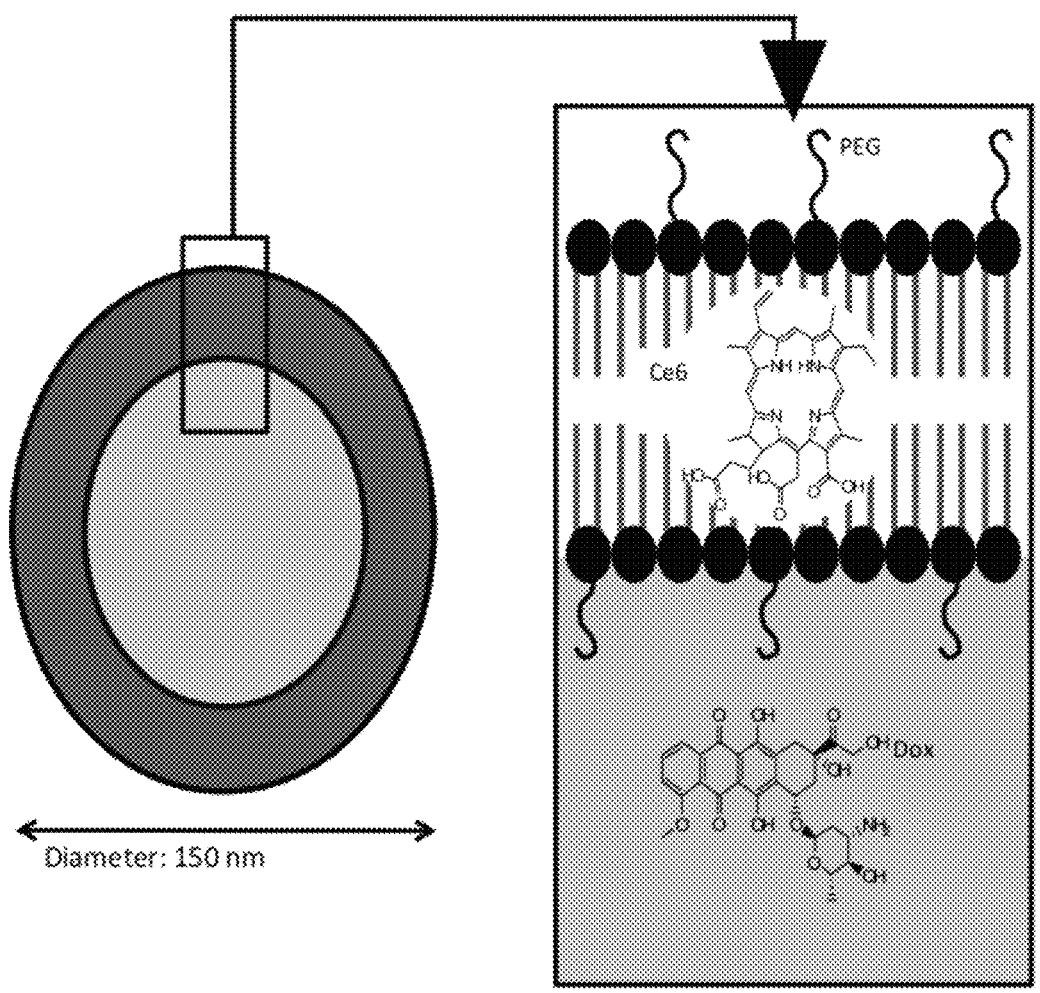
FIG. 1 shows a diagram of dual-effect liposome and its particle size. (A) Dual-effect liposome encapsulates doxorubicin into the interior and Ce6 into the lipid bilayer. (B) Particle size of dual-effect liposome.
Figure 1:
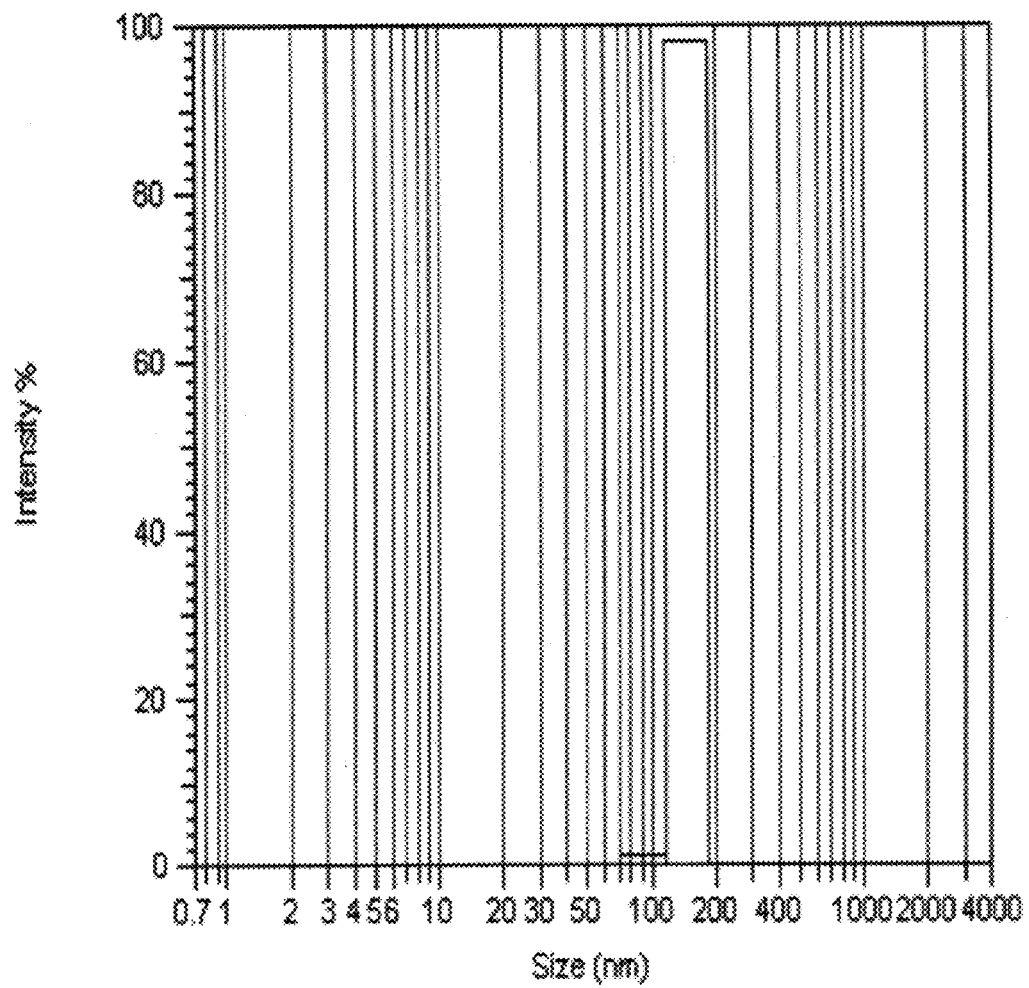

The invention unexpectedly found that a liposome encapsulating a photosensitizer and a drug such as an anti-tumor drug (dual-effect liposome) simultaneously will enhance the release and accumulation of the drug at the target site after a photodynamic process. Surprisingly, the invention found that in the photodynamic process, one administration with one dose of the dual-effect liposome and at least one time of irradiation (preferably at least two times) can achieve superior therapy effect. For example, it can almost completely eliminate tumors. On the contrary, the conventional chemotherapy needs multi-administration and multi-doses in therapeutic regimen but still cannot achieve tumor free effect.

Unless defined otherwise, all the technical and scientific terms used herein have the same meaning as is commonly understood by one of ordinary skill in the art. All patents, applications, published applications and other publications are incorporated by reference in their entirety. In the event that there is a plurality of definitions of a term, those in this section prevail unless stated otherwise.

As used herein, "tumor" denotes a neoplasm, and includes both benign and malignant tumors. This term particularly includes malignant tumors which can be either solid or non-solid. Tumors can also be further divided into subtypes, such as adenocarcinomas.

As used herein, "target" denotes the object that is intended to be detected, diagnosed, impaired or destroyed by the methods provided herein, and includes target cells and target tissues. "Target tissues" and "target cells" as used herein are tissues that are intended to be impaired or destroyed by this treatment method. Photosensitizing compounds bind to these target tissues or target cells; then, when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included in target cells are cells undergoing substantially more rapid division as compared to non-target cells.

As used herein, "non-target tissues" are all the tissues of the subject which are not intended to be impaired or destroyed by the treatment method. These non-target tissues include but are not limited to healthy blood cells, and other normal tissue not otherwise identified as targeted.

As used herein, a "therapeutically effective dose" is a dose sufficient to prevent advancement or cause regression of a disease, or which is capable of relieving symptoms caused by the disease As used herein, "irradiating" and "irradiation" include exposing a subject to all wavelengths of light. Preferably, the irradiating wavelength is selected to match the wavelength(s) which excite(s) the photosensitive compound. Preferably, the radiation wavelength matches the excitation wavelength of the photosensitive compound and has low absorption by the non-target tissues of the subject, including blood proteins. Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. The radiation energy is provided by an energy source, such as a laser or cold cathode light source which is external to the subject, implanted in the subject, or introduced into a subject, such as by a catheter, optical fiber or by ingesting the light source in capsule or pill form (e.g., as disclosed in. U.S. Pat. No. 6,273,904 (2001))

As used herein, "eliminate" means to kill the desired target tissue or target cell. "Impair" means to change the target tissue or target cell in such a way as to interfere with its function or reduce its growth.

As used herein, "mammals" or "mammalian subject" includes farm animals, such as cows, hogs and sheep, as well as pet or sport animals such as horses, dogs, and cats.

The invention provides a method for photodynamic therapy in target tissues in a subject, comprising (a) administering a therapeutically effective dose of liposome containing a photosensitizer and a drug to a subject and (b) irradiating the target tissues at least one time at appropriate time(s). Preferably, the irradiation is performed at least two times.

According to the invention, after administering a liposome containing a photosensitizer and a drug to a subject, performing an irradiation to the target tissues at least one time at appropriate time(s) will produce advantageous treatment effect. Preferably, the target tissue is tumor tissue. More preferably, the tumors can be almost completely eliminated.

According to the invention, the administration is rectal, nasal, vaginal parenteral or topical. More preferably, the administration is parenteral including but not limited to intravenous, subcutaneous, intramuscular, intradermal and intraperitoneal. More preferably, the administration is intravenous.

According to the invention, after administering liposomes containing a photosensitizer and an anti-tumor drug to a subject, the liposomes will reach the tumor sites and subsequently accumulate at the tumor sites to an appropriate amount. Preferably, the amount is a maximum amount. The inventors unexpectedly found that when liposomes reach target sites, performing an irradiation to the liposomes will increase the accumulation of the drug at the target sites. When the accumulation of the at the tumor sites reaches an appropriate amount, performing other irradiation will produce advantageous anti-tumor effect. Preferably, the amount is a maximum amount. In one embodiment, the invention provides a method for therapy in target tissues in a subject, comprising (a) administering a therapeutically effective dose of liposome containing a photosensitizer and a drug to a subject, (b) performing a first irradiation to the tumor tissues at the time the drug reaches the tumors, (c) performing a second irradiation to the tumor tissues at the time the drug accumulates at the target tissues to a maximum amount, and optionally (d) performing other irradiations to the target tissues. Preferably, the amount is a maximum amount. Preferably, the administration is rectal, nasal, vaginal parenteral or topical. More preferably, the administration is parenteral including but not limited to intravenous, subcutaneous, intramuscular, intradermal and intraperitoneal. More preferably, the administration is intravenous. Preferably, the targets are tumors. Preferably, the drug is an anti-tumor drug.

According to the invention, when to perform the first irradiation can be determined by intravenously pre-administering a liposome containing a photosensitizer and a drug to a subject under a condition of evading light and measuring when the drug reaches the targets. The time of performing the second irradiation is determined by measuring the appropriate amount of accumulation of the drug after the first irradiation. Preferably, the target tissue is tumor tissue. More preferably, the tumors can be almost completely eliminated. Preferably, the amount is a maximum amount.

According to the invention, more than two irradiations can be performed depending on the necessity of the therapy.

To enhance the efficacy of treatment, the invention develops a liposome encapsulated with a photosensitizer and a drug. Here such a liposome is named as dual-effect liposome. This dual-effect liposome is developed not only to kill target cells using PDT but also to accelerate the drug release from the liposome. The photosensitizer and the drug can be encapsulated in the lipid bilayer or aqueous interior, depending on the hydrophobic or hydrophilic property of the photosensitizer and the drug.

According to the invention, a liposome is a generic term encompassing a variety of single- and multi-lamellar lipid vehicles formed by the generation of enclosed lipid bilayers or aggregates. Liposomes may be characterized as having vesicular structures with a bilayer membrane, generally comprising a phospholipid, and an inner medium. Liposomes can range in size from several nanometers to several micrometers in diameter. A liposome used according to the invention can be made with different methods, as would be known to one of ordinary skill in the art. Illustrative examples of phospholipids for the preparation of liposome include lecithin, sphingomyelin, dipalmitoylphosphatidyl-choline, etc. Representative steroids include cholesterol, chlorestanol, lanosterol, and the like. Representative charge amphiphilic compounds generally contain 12 to 30 carbon atoms. Mono- or dialkyl phosphate esters, or alkylamines, e.g. dicetyl phosphate, stearyl amine, hexadecyl amine, dilaurylphosphate, and the like are representative. The liposome sacs can be prepared by vigorous agitation in the solution. Further details with respect to the preparation of liposomes are set forth in U.S. Pat. No. 4,342,826 and PCT International Publication No. WO 80/01515, both of which are incorporated by reference.

According to the invention, any suitable drug can be used in methods of the invention. Preferably, the drug is an anti-tumor drug and any appropriate anti-tumor drug can be used in the invention. The suitable candidates include, but are not limited to: a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine); b) antimetabolite drugs (such as 5-fluorouracil, cytarabine, gemcitabine, purine analogues such as pentostatin, methotrexate); c) alkylating agents or nitrogen mustards (such as nitrosoureas, cyclophosphamide or ifosphamide); d) drugs which target DNA such as the antracycline drugs adriamycin, doxorubicin, pharmorubicin or epirubicin; e) drugs with target topoisomerases such as etoposide; f) hormones and hormone agonists or antagonists such as estrogens, antiestrogens (tamoxifen and related compounds) and androgens, flutamide, leuprorelin, goserelin, cyprotrone or octreotide; g) drugs which target signal transduction in tumour cells including antibody derivatives such as herceptin; h) alkylating drugs such as platinum drugs (cis-platin, carbonplatin, oxaliplatin, paraplidineatin) or nitrosoureas; i) drugs potentially affecting metastasis of tumours such as matrix metalloproteinase inhibitors; j) gene therapy and antisense agents; k) antibody therapeutics; l) other bioactive compounds of marine origin, notably kahalalide F or the ecteinascidins such as et-743; m) other drugs which combat side effects of aplidine such as antiemetics; o) more generally drugs which allow aplidine to be dosed at the Recommended Dose and manage toxicity.

According to the invention, any appropriate photosensitizer can be used in the invention. Photosensitizers include, but are not limited to, hematoporphyrins, such as hematoporphyrin HCl and hematoporphyrin esters; dihematophorphyrin ester; hematoporphyrin IX and its derivatives; 3,1-meso tetrakis (o-propionamidophenyl) porphyrin; hydroporphyrins such as chlorin, herein, and bacteriochlorin of the tetra (hydroxyphenyl) porphyrin series, and synthetic diporphyrins and dichlorins; o-substituted tetraphenyl porphyrins (picket fence porphyrins); chlorin e6; Npe6; mono-ethylendiamine monamide; mono-1-aspartyl derivative of chlorin e6, and mono- and diaspartyl derivatives of chlorin e6; the hematoporphyrin mixture Photofrin II; benzophorphyrin derivatives (BPD), including benzoporphyrin monoacid Ring A (BPD-MA), tetracyanoethylene adducts, dimethyl acetylene dicarboxylate adducts, Diels-Adler adducts, and monoacid ring "a" derivatives; a naphthalocyanine; toluidine blue O; aluminum sulfonated and disulfonated phthalocyanine ibid.; and phthalocyanines without metal substituents, and with varying other substituents; a tetrasulfated derivative; sulfonated aluminum naphthalocyanines; methylene blue; nile blue; crystal violet; azure β chloride; toluidine blue; and rose bengal. The photosensitizer used in the invention is preferably hematoporphyrin, chlorine e6, Npe6, toluidine blue, Rose Bengal, or methylene blue.

Other potential photosensitizers include, but are not limited to, pheophorbides such as pyropheophorbide compounds, anthracenediones; anthrapyrazoles; aminoanthraquinone; phenoxazine dyes; phenothiazine derivatives; chalcogenapyrylium dyes including cationic selena- and tellura-pyrylium derivatives; verdins; purpurins including tin and zinc derivatives of octaethylpurpurin and etiopurpurin; benzonaphthoporphyrazines; cationic imminium salts; and tetracyclines.

In view of the above, the invention specifically provides a liposome composition, comprising liposome, a photosensitizer Ce6 or Npe6 and an anti-cancer drug, wherein the photosensitizer and the anti-cancer drug are encapsulated within the liposome and wherein the ratios of the liposome and photosensitizer are 60-90% and 0.2-1.8% (w/w), respectively. Preferably, the photosensitizer is encapsulated within lipid bilayer of the liposome. Preferably, the anti-cancer drug is doxorubicin or cisplatin. Preferably, the ratios of the liposome, the photosensitizer and the anti-cancer drug are 60-90%, 0.2-1.8% and 0.9-10% (w/w), respectively. More preferably, the ratios of the liposome, the photosensitizer and the anti-cancer drug are 70-90% (preferably 80%), 0.2-1.6% and 0.9-10% (w/w), respectively.

In one embodiment, the ratios of the liposome and Ce6 are 75-85% and 0.3-0.6%, respectively. Preferably, the ratios of the liposome, Ce6 and cisplatin are 75-85%, 0.3~0.6% and 0.8~1.5% (w/w), respectively. Preferably, the ratios of the liposome, Ce6 and cisplatin are 75-85%, 0.3~0.6% and 0.8~1.5% (w/w), respectively. In another embodiment, the ratios of the liposome, Ce6 and doxorubicin are 75-85%, 0.5-1.6% and 5.5-6.5% (w/w), respectively. In another embodiment, the ratios of the liposome and Npe6 are 75-85% and 0.5-1.3%, respectively. Preferably, the ratios of the liposome, Npe6 and doxorubicin are 75-85%, 0.5~1.3% and 8.5~9.5% (w/w), respectively. In another embodiment, the ratios of the liposome, Npe6 and cisplatin are 75-85%, 0.3~1.5% and 0.8~1.5% (w/w), respectively.

The photosensitizers of the invention are illuminated/irradiated, i.e. activated, using conventional techniques known in the field of photodynamic inactivation. Preferably, the photosensitizers are illuminated/irradiated at a wavelength between 400 nm and 800 nm. More preferably, the photosensitizers are illuminated/irradiated at a wavelength corresponding to one or more of the absorption windows for porphyrin, which lie at around 417 nm (Soret band), 485 nm, 515 nm, 550 nm, 590 nm and 650 nm. Illumination/irradiation of the appropriate wavelength for a given compound can be administered by a variety of methods. These methods include but are not limited to the administration of laser, nonlaser, or broadband light. Irradiation can be produced by extracorporeal or intraarticular generation of light of the appropriate wavelength.

According to the invention, the tumors to be treated are preferably solid tumors. More preferably, the tumors to be treated are selected from sarcomas, carcinomas, and lymphomas. Examples of such tumors are bladder cancer, melanoma, breast cancer, non-Hodgkin's lymphoma, brain cancer, bone cancer, colon and rectal cancer, liver cancer, pancreatic cancer, endometrial cancer, prostate cancer, kidney cancer, skin cancer (non-melanoma), thyroid cancer, and lung cancer (small cell lung cancer and non small cell lung cancer).

By using the method of the invention, the tumors can be almost completely eliminated. This cannot be achieved by any photodynamic therapy known in the art.

EXAMPLE

Example 1 Preparation of Dual-Effect Liposome of the Invention

Preparation of Liposome-Ce6 (Lipo-Ce6)

1,2-Distearoyl-sn-Glycero-3-phosphatylcholine (DSPC), cholesterol and DSPC-polyethylene glycol (PEG) were mixed in an organic solvent at a molar ration of 50:25:1. 15.2 μmol of the resulting solution and 0.2 mg of Ce6 were mixed and then subjected to vacuum evaporator at 65 rpm and a temperature of 65° C. for 30 minutes to form a thin film around the flask. 250 nM ammonium sulfate solution was preheated to 65° C. and 1 ml of the ammonium sulfate solution was added to the flask. Then, the flask was shaken in water bath-type sonicator for 20 minutes for hydration. The resulting solution was frozen with liquid nitrogen and thawed with 65° C. water. The above frozen-thawing cycle was performed for 5 times. The resulting solution was filtrated and subjected to Sephadex G-50 column to remove free form Ce6, so that the Ce6-containing liposome solution (Lipo-Ce6) was obtained. The size of the resulting Lipo-Ce6 was around 151.1+/−32.5 nm.

Preparation of Liposome-Doxorubicin-Ce6 (Lipo-Dox-Ce6)

Lipo-Ce6 and doxorubicin (Dox) (1 mg/0.1 ml) were individually preheated to 65° C. They were mixed and reacted for 30 minutes under water bath (Hotech Instruments Corp.) at 65° C. The resulting solution was cooled with ice water and then subjected to Sephadex G-50 column to remove free form doxorubicin, so that the doxorubicin-containing Lipo-Ce6 solution (Lipo-Dox-Ce6) was obtained. The size of the resulting Lipo-Dox-Ce6 was around 152.9+/−37.7 nm (see FIGS. 1 (A) and (B)).

Quantitative Analysis of Ce6 in Lipo-Ce6 and Lipo-Dox-Ce6

A serial dilution was made for 4 mg/ml of Ce6 stock solution to obtain 2 μg/ml, 1 μg/ml, 0.5 μg/ml, 0.25 μg/ml, 0.125 μg/ml and 0.0625 μg/ml of solutions. A checking-measuring curve was made on the basis of the above concentrations and the absorption values of these dilution solutions at 400 nm measured by UV-Visible spectrophotometer (Horiba Jobin Yvon). Lipo-Ce6 and Lipo-Dox-Ce6 were diluted 100 times with 95% alcohol and their absorption values at 400 nm were also measured by UV-Visible spectrophotometer (Horiba Jobin Yvon).

Quantitative Analysis of Dox in Lipo-Ce6 and Lipo-Dox-Ce6

10 mg/ml of Dox stock solution was performed serial dilution to 10 μg/ml, 5 μg/ml, 2.5 μg/ml, 1.25 μg/ml, 0.625 μg/ml and 0.3125 μg/ml to make checking-measuring curve and the absorption values of these dilution solutions at 470 nm were measured by UV-Visible spectrophotometer (Horiba Jobin Yvon). Lipo-Dox-Ce6 were diluted 100 times with 95% alcohol and its absorption values at 470 nm were also measured by UV-Visible spectrophotometer (Horiba Jobin Yvon).

Stability of Lipo-Dox-Ce6

To investigate stability of Lipo-Dox-Ce6, the prepared Lipo-Dox-Ce6 was stored under light-evading conditions. The amounts of Ce6 and Dox of Lipo-Dox-Ce6 were measured at 0, 1, 3, 7, 14, 21, 30 and 60 days. It was found that after 60 days, the particle size of Lipo-Dox-Ce6 remained at around 155 nm and Dox and Ce6 did not significantly decrease in 21 days. Even at 60 days, Dox and Ce6 decreased by only around 10%.

Preparation of Liposome-Ce6-Cisplatin (Lipo-Ce6-cDDP) and Liposome-Npe6-Dox (Lipo-Npe6-Dox)

The Lipo-Ce6-cDDP and Lipo-Npe6-Dox were prepared according to the procedures of preparing Lipo-Dox-Ce6 mentioned above.

Figure 7:
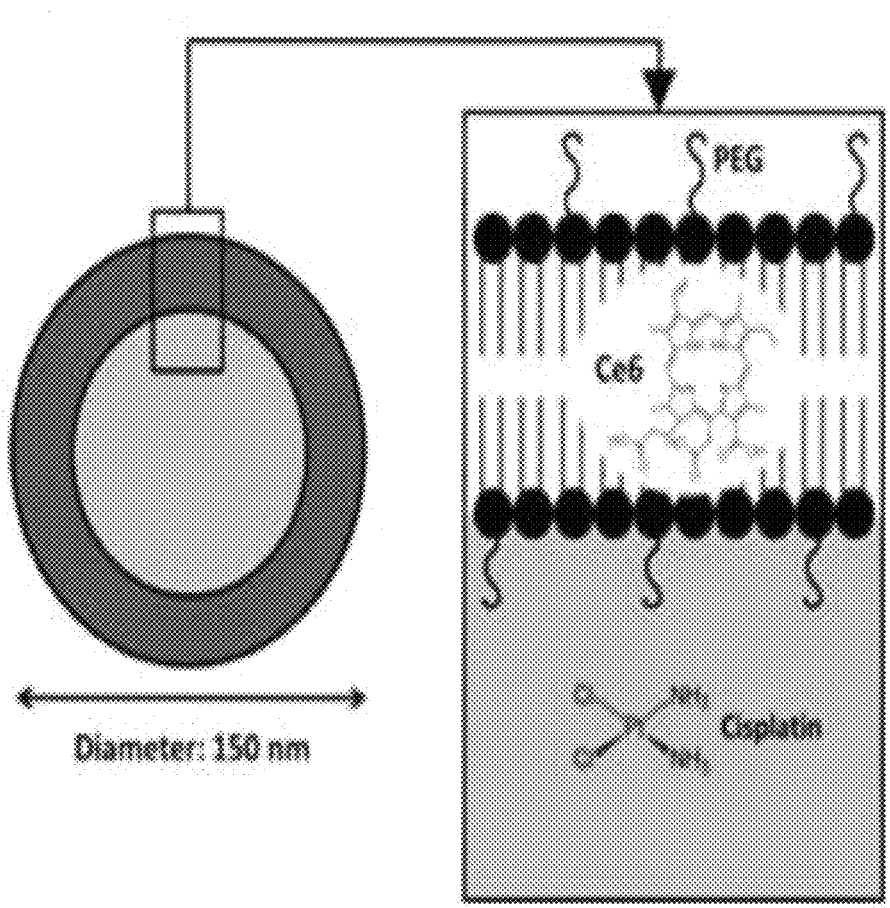
FIG. 7 shows schematic illustration of dual effect liposome (FIG. 7 (A)) and particle size of liposomal-Ce6-cDDP (FIG. 7 (B)).
Figure 7:
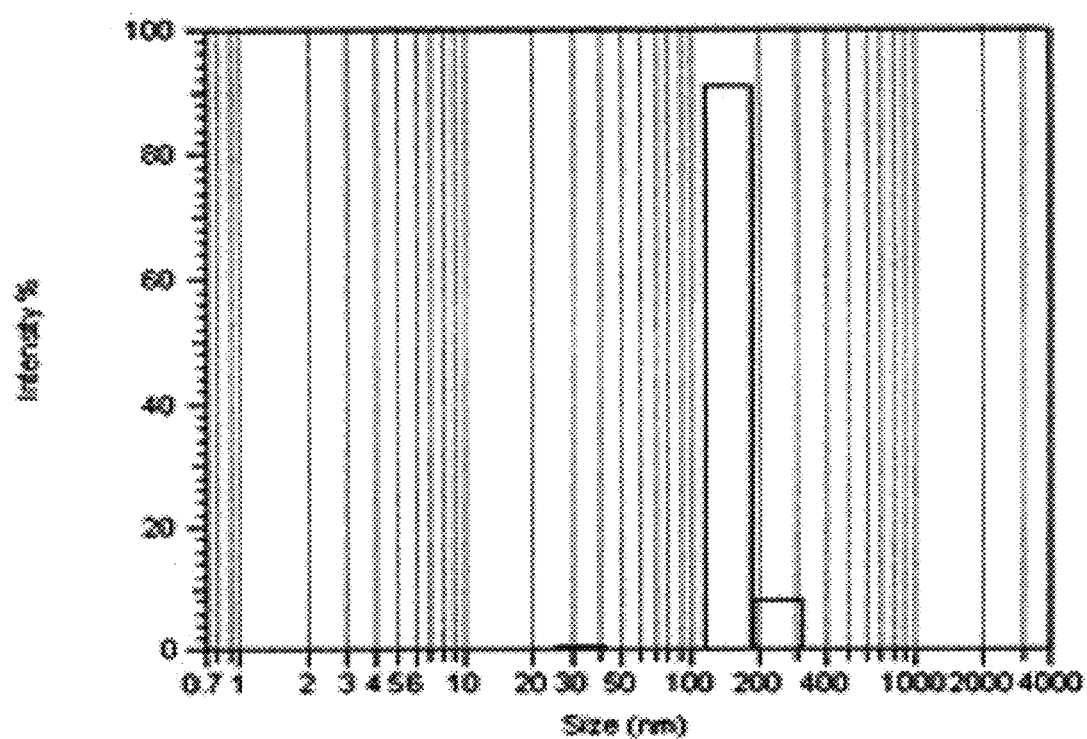

The schematic illustration of dual effect liposome Lipo-Ce6-cDDP and the particle size of Lipo-Ce6-cDDP are shown in FIGS. 7 (A) and (B). The entrapment efficiencies of Ce6 and cDDP in Lipo-Ce6-cDDP are listed in the below table:

| | Particle size (nm) | Lipid recovery % | Ce6 entrapment (ug/umole) | Ce6 entrapment efficiency (%) | cDDP entrapment (ug/umole) | cDDP entrapment efficiency (%) |
|---|---|---|---|---|---|---|
| Lipo-Ce6-cDDP | 155.1 | 82.4 | 8.5 | 86.4 | 12.6 | 16 |

The stability of Lipo-Ce6-cDDP is listed in the below table:

| | Days | | | | | | | |
|---|---|---|---|---|---|---|---|---|
| | 0 | 1 | 3 | 7 | 14 | 21 | 30 | 60 |
| Leakage of Ce6 (%) | 0.00 | 2.7 +/− 1.1 | 5 +/− 1.9 | 5.5 +/− 2.1 | 4.9 +/− 2.2 | 9.1 +/− 2.7 | 11.1 +/− 1.7 | 12.5 +/− 1.5 |

-continued

| | Days | | | | | | | |
|---|---|---|---|---|---|---|---|---|
| | 0 | 1 | 3 | 7 | 14 | 21 | 30 | 60 |
| Leakage of cDDP (%) | 0.00 | 4.8 +/− 0.6 | 5.7 +/− 1 | 5.8 +/− 1.8 | 8.3 +/− 1.8 | 6.8 +/− 1.7 | 10.2 +/− 0.9 | 12.4 +/− 0.9 |
| Particle size (nm) | 148 +/− 10 | | | 145 +/− 5 | 148 +/− 9 | 150 +/− 7 | 150 +/− 9 | 150 +/− 14 |

Example 2 In Vivo Photodynamic Therapy Assay for Lipo-Dox-Ce6

Profile of Dox in Tumors after Intravenously Injection of Lipo-Dox-Ce6

The cells of mouse colon adenocarcinoma cell line, Colon-26 (C-26), were incubated in RPMI 1640 medium containing 10% FBS at 37° C. $2 \times 10^5$ cells in 50 μl RPMI 1640 medium without phenol red were subcutaneously implanted into the back of male BALB/c mice. After the cells grew to 100 mm$^3$, Lipo-Dox-Ce6 were intravenously injected to tails of the mice. After 2, 6, 12, 24 and 48 hours of light evasion, the mice were sacrificed. The blood and tumor tissues in the mice were collected. The phosphate buffer was added to the blood and tumor tissues and then they were individually homogenized by homogenizer (Biospec Products, Inc.). 95% ethanol with 0.6 N HCl was added to the homogenized solutions, which were then placed at 4° C. overnight. The resulting solutions were centrifuged at 12000 rpm for 15 minutes. The supernatants were collected and the amounts of Ce6 and Dox were measured by UV-Visible spectrophotometer (Horiba Jobin Yvon), respectively.

Figure 2:
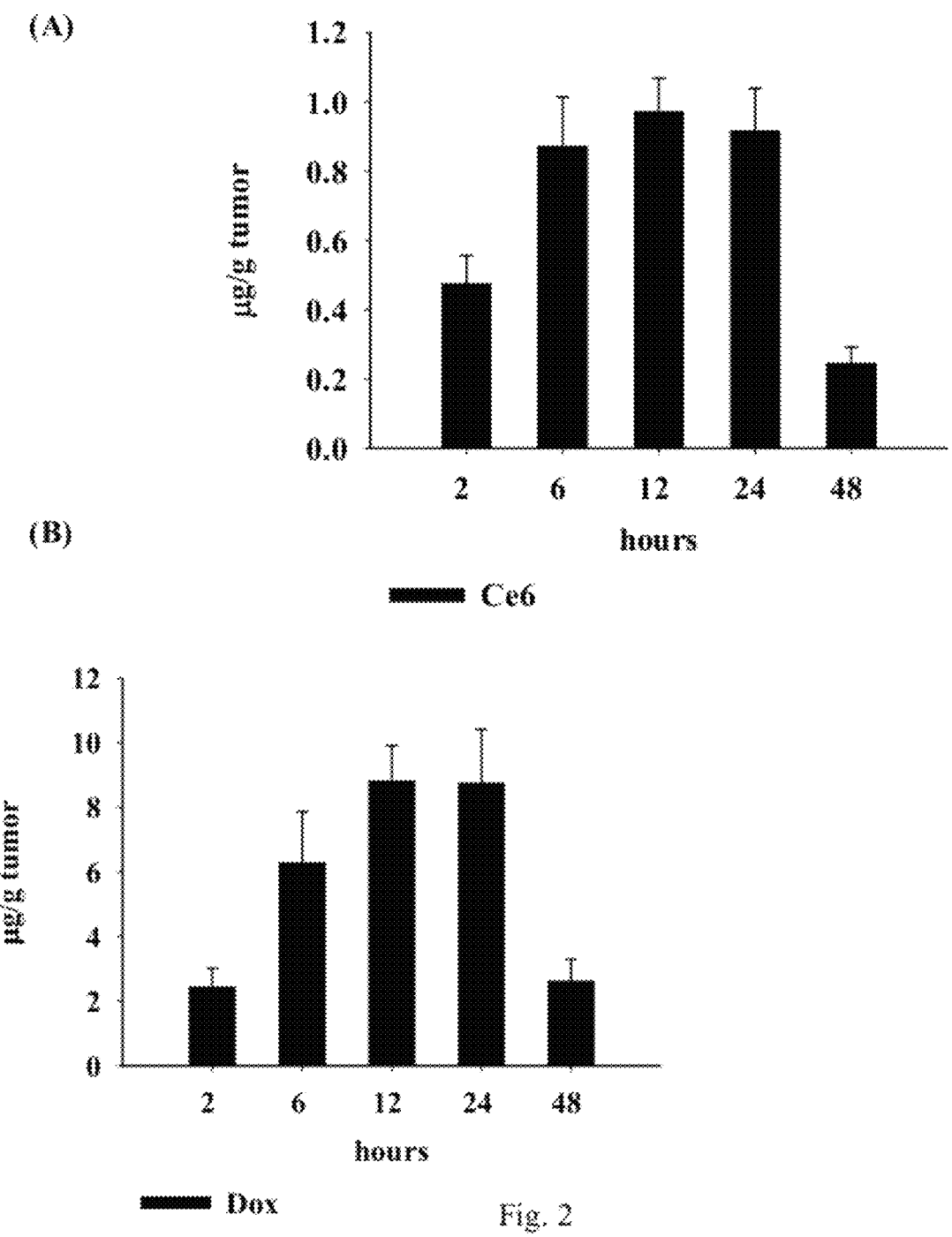
FIG. 2 shows the accumulation of Ce6 (FIG. (A)) and Dox (FIG. (B)) in tumor tissues of mice.
Figure 3:
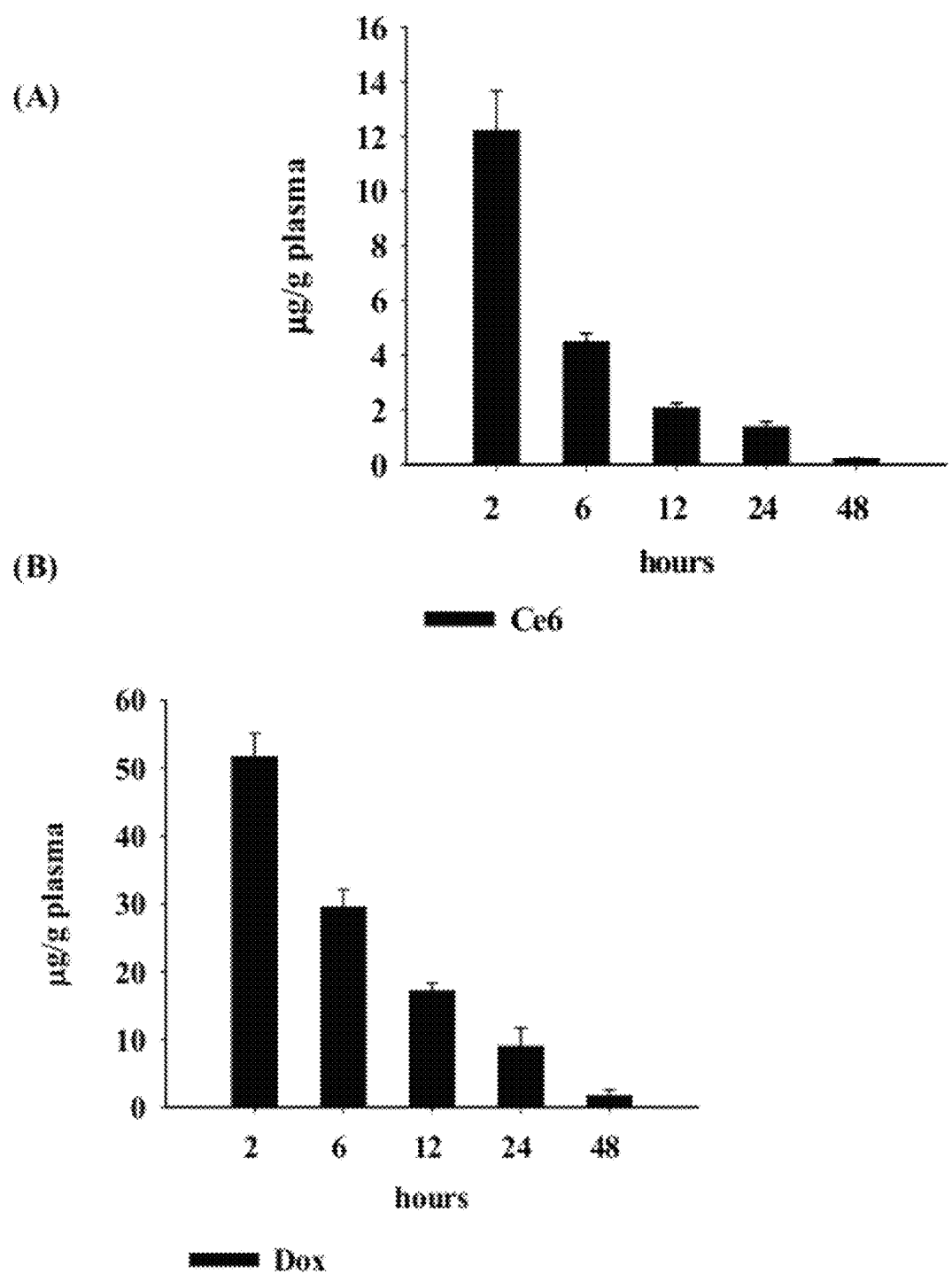
FIG. 3 shows the distribution of Ce6 (FIG. 3 (A)) and Dox (FIG. 3 (B)) in the blood of mice.

As shown in FIG. 2, the accumulation of Ce6 (FIG. (A)) and Dox (FIG. (B)) in tumor tissues reached the maximum amount after 12 hours and gradually reduced after 24 hours. On the other hand, Ce6 and Dox distribution in the blood reached the maximum amount right after the injection. Subsequently, Ce6 and Dox gradually were metabolized and distributed to various tissues, so the amount of Dox in blood was reduced (see FIGS. 3 (A) and 3 (B)).

One-Time Photodynamic Therapy after Two Hours or Twelve Hours

The cells of mouse colon adenocarcinoma cell line, Colon-26 (C-26), were incubated in RPMI 1640 medium containing 10% FBS at 37° C. $2 \times 10^5$ cells in 50 μl RPMI 1640 medium without phenol red were subcutaneously implanted into the back of male BALB/c mice. After the cells grew to 100 mm$^3$, Lipo-Dox-Ce6 were intravenously injected to tails of the mice. The mice were evenly divided to three groups (10 mice in each group). The three groups were subjected to photodynamic therapy with no irradiation, with irradiation after 2 hours of injection and with irradiation after 12 hours of injection, respectively. Another group having the same number of mice (10) was injected with 0.9% NaCl and used as the control group. The irradiation was conducted with the light source (Laser Diode) having the strength of 105 mW/cm$^2$ and wavelength of 662 nm and the irradiation dose of 100 J/cm$^2$. The tumor sizes were measured by Electronic Digital Caliper every three days in accordance with the formula: tumor volume=½ (shortest side of the tumor)$^2$×the longest side.

Figure 4:
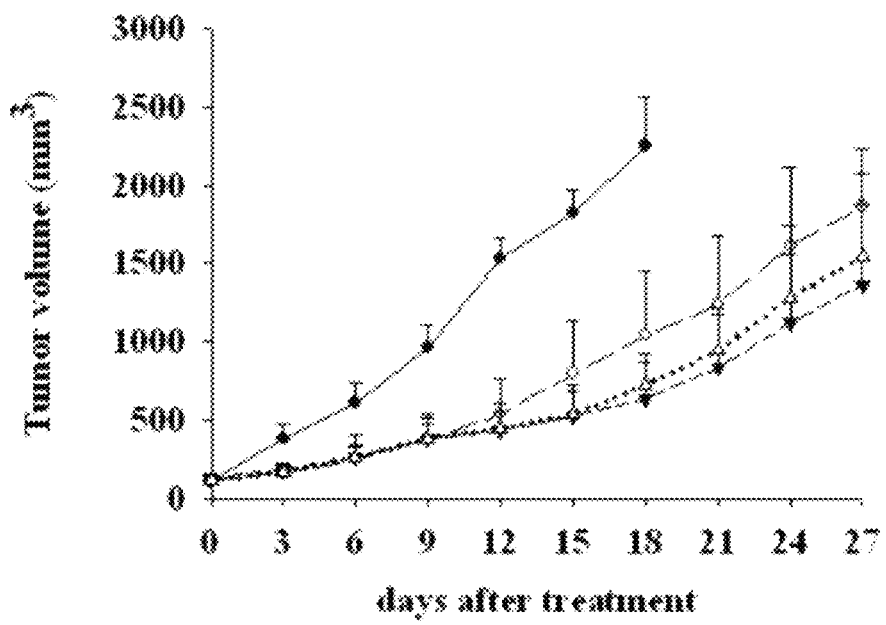
FIG. 4 shows one dose of dual-effect liposome (Ce6: 1.75 mg/kg; Dox: 8.03 mg/kg) administrated into BALB/cByJ mouse inoculated with at C26 mouse colon cancer cells through tail vein injection, 2 hr and 12 hr later after drug administration, light irradiation. (A) Tumor growth inhibition curve and (B) Kaplan-Meier survival plot of BALB/cByJ mice bearing subcutaneous C-26 tumor. Mice received PBS (untreated), dual-effect liposome loaded with Ce6 and doxorubicin without light exposure (Lipo-Ce6-Dox), and dual-effect liposome loaded with Ce6 and doxorubicin plus light exposure 2 hr (Lipo-Ce6-Dox-2h) and 12 hr (Lipo-Ce6-Dox-12h) after liposome administration. Tumors were measured and animal survival were monitored every three days until day 27 or tumor volume ≥2000 mm3. Data as mean±SD (n=7-10 mice).
Figure 4:
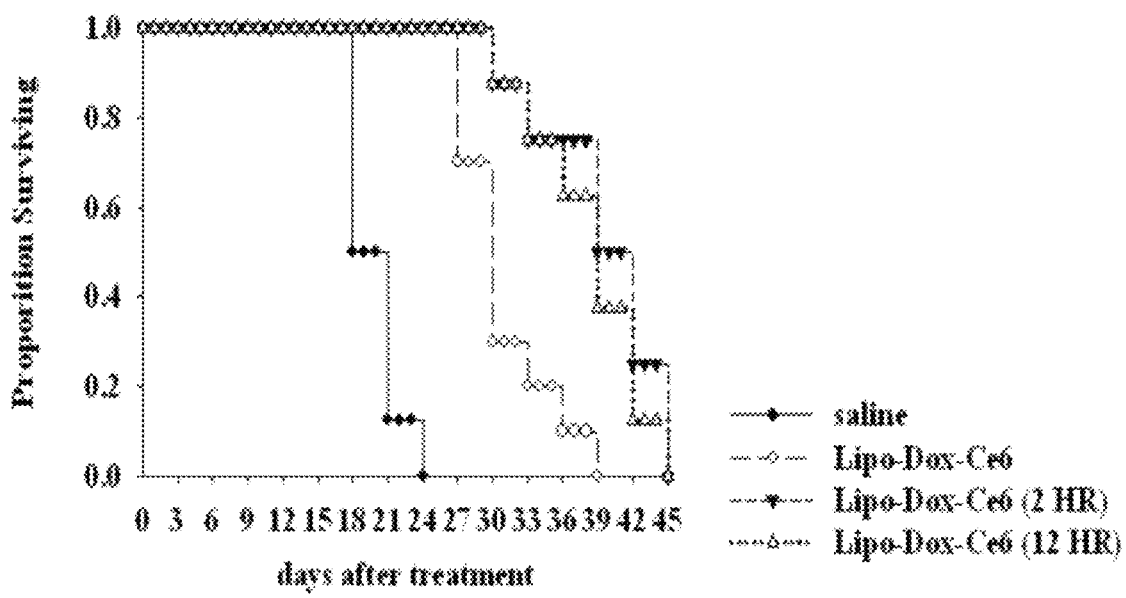

As shown in FIG. 4, the photodynamic therapy conducted at the 2 hours will increase Dox accumulation in tumor tissues at 12 hours and the results prove that the dual effect liposome after photodynamic therapy enhances Dox accumulation in tumor tissues.

More Times of Photodynamic Therapy after Two and Twelve Hours

Figure 5:
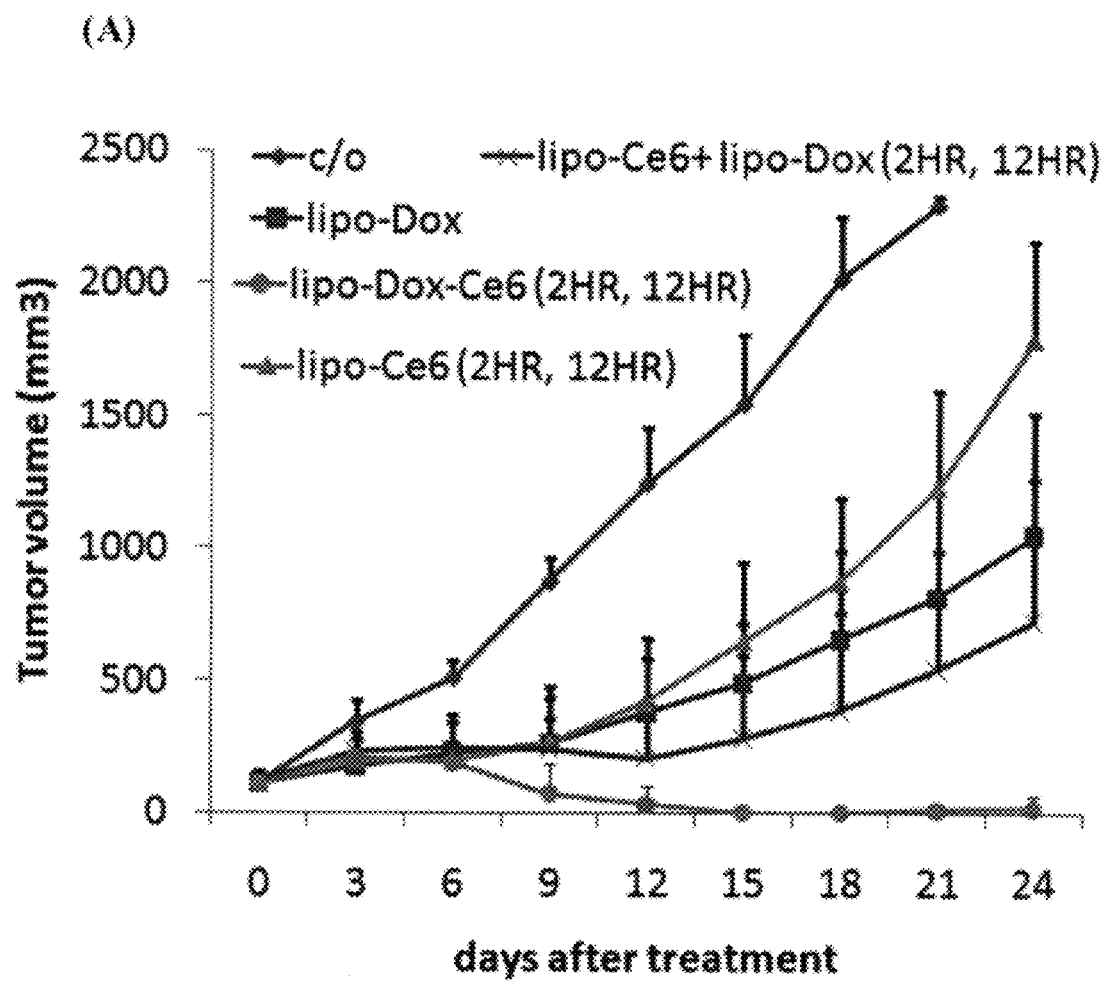
FIG. 5 shows one dose of dual-effect liposome (Ce6: 1.75 mg/kg; Dox: 8.03 mg/kg) administrated into BALB/cByJ mouse inoculated with at C26 mouse colon cancer cells through tail vein injection. Two doses of light (100 J/cm2) were applied onto the tumor at 2 and 12 hr post drug administration. (A) tumor size. (B) Survival rate (N=10).
Figure 5:
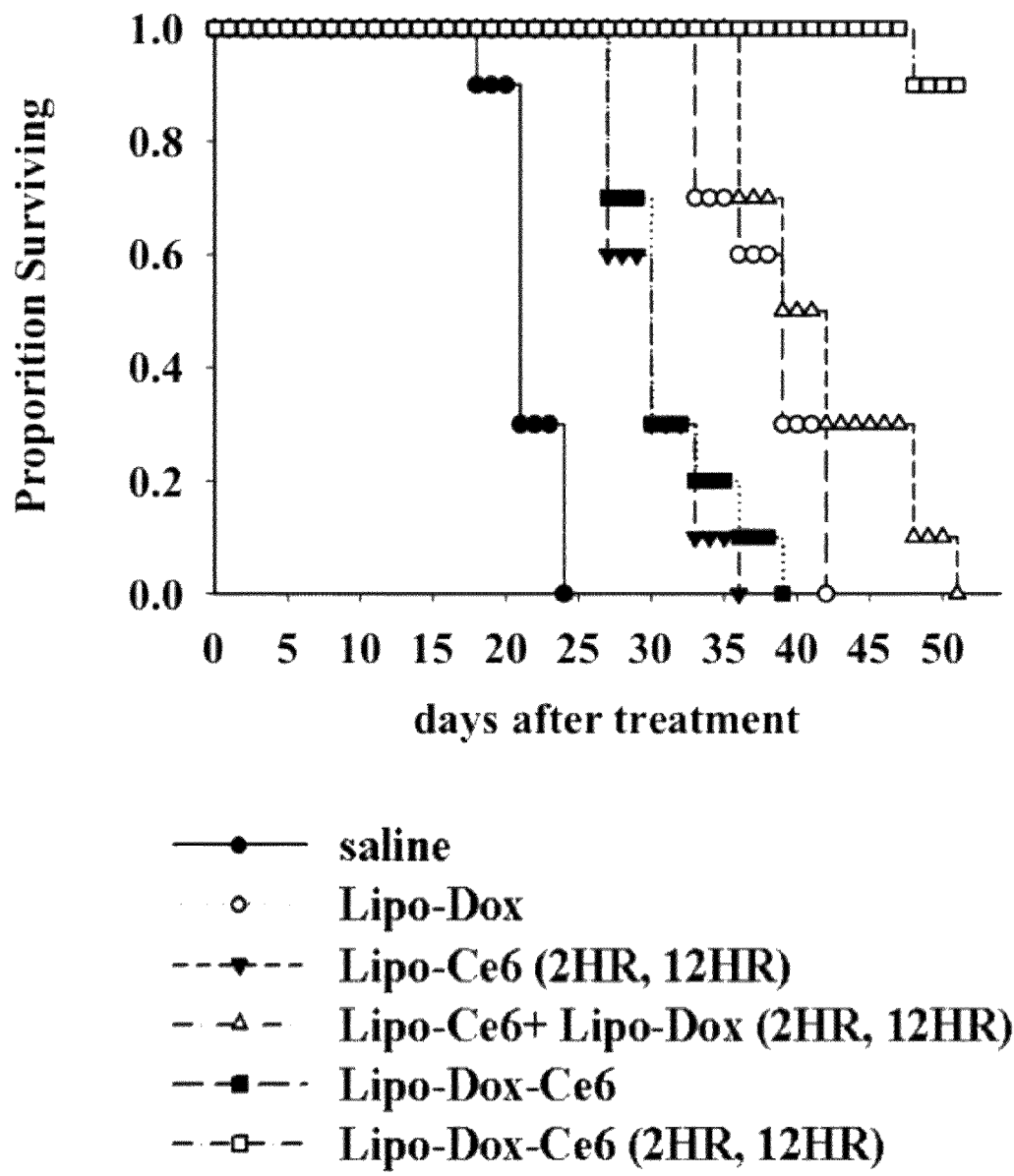
Figure 6:
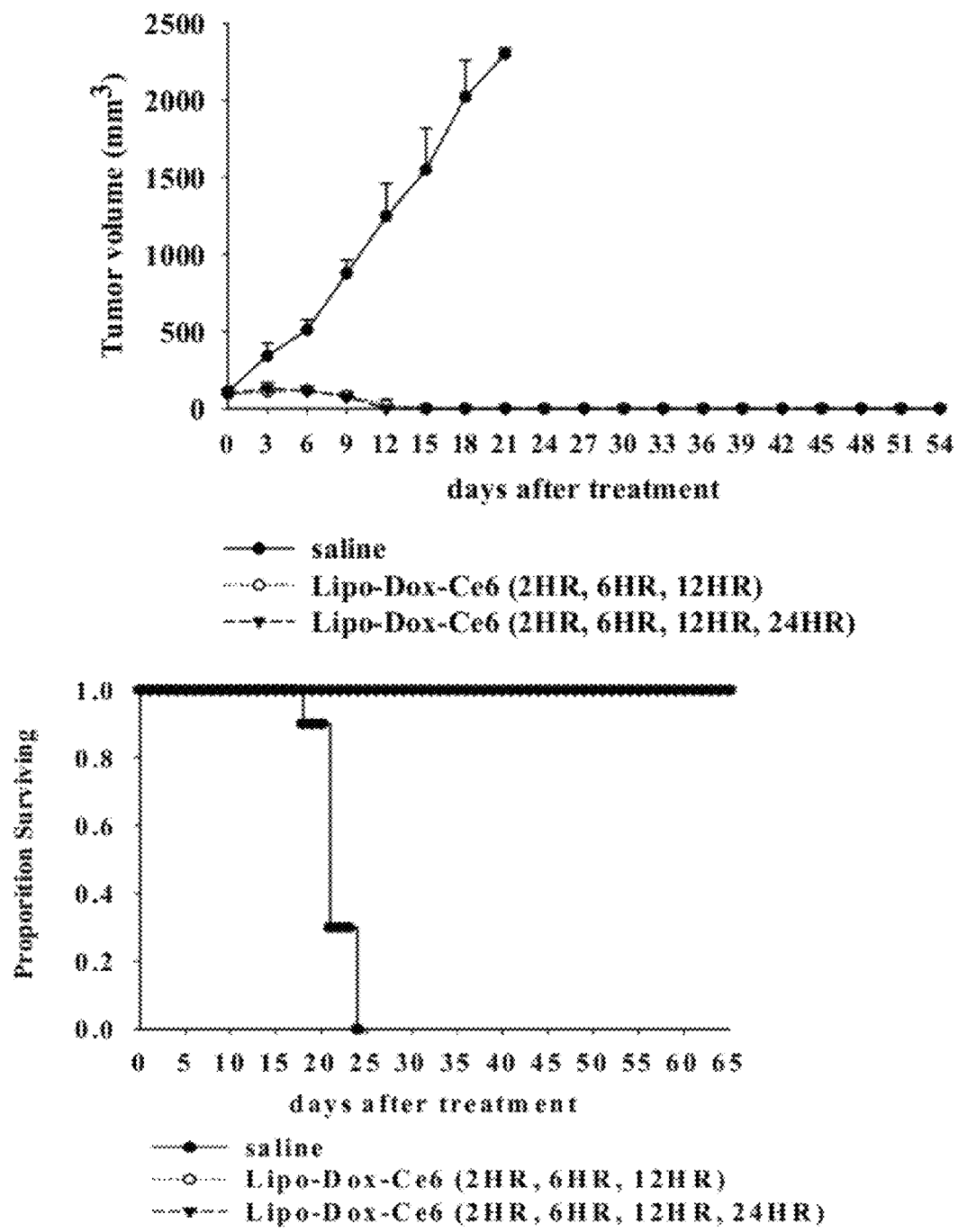
FIG. 6 shows one dose of dual-effect liposome (Ce6: 1.75 mg/kg; Dox: 8.03 mg/kg) administrated into BALB/cByJ mouse inoculated with at C26 mouse colon cancer cells through tail vein injection. Three and four doses of light (100 J/cm2) were applied onto the tumor at 2, 6, 12 and 24 hr post drug administration. (A) tumor size. (B) Survival rate (N=10).

Mouse colon adenocarcinoma cell line, Colon-26 (C-26), were subcutaneously implanted into BALB/c mice. After the tumor grew to 100 mm$^3$, Lipo-Dox, Lipo-Ce6 and Lipo-Dox-Ce6 were intravenously injected to tails of the mice, respectively. The mice were evenly divided to three groups (10 mice in each group). Each group was subjected to photodynamic therapy with irradiation after 2 and 12 hours of injection, respectively. The control group was injected with 0.9% NaCl. The irradiation was conducted with the light source (Laser Diode) having strength of 105 mW/cm$^2$ and wavelength of 662 nm and the irradiation dose of 100 J/cm$^2$. The tumor sizes were measured by Electronic Digital Caliper every three days in accordance with the formula: tumor volume=½ (shortest side of the tumor)$^2$×the longest side. As shown in FIG. 4 (A), the Lipo-Dox-Ce6 group reduced more tumor volume than the Lipo-Ce6+Lipo-Dox group, the Lipo-Dox group and the Lipo-Ce6 group. Particularly, the tumors were completely eliminated in the group receiving Lipo-Dox-Ce6 and irradiated at 2 and 12 hours (FIG. 5). Further experiments with irradiation for three times at 2, 6 and 12 hours and four times at 2, 6, 12 and 24 hours were performed and the results are shown in FIG. 6.

Example 3 In Vitro Cytotoxicity Assay

Figure 8:
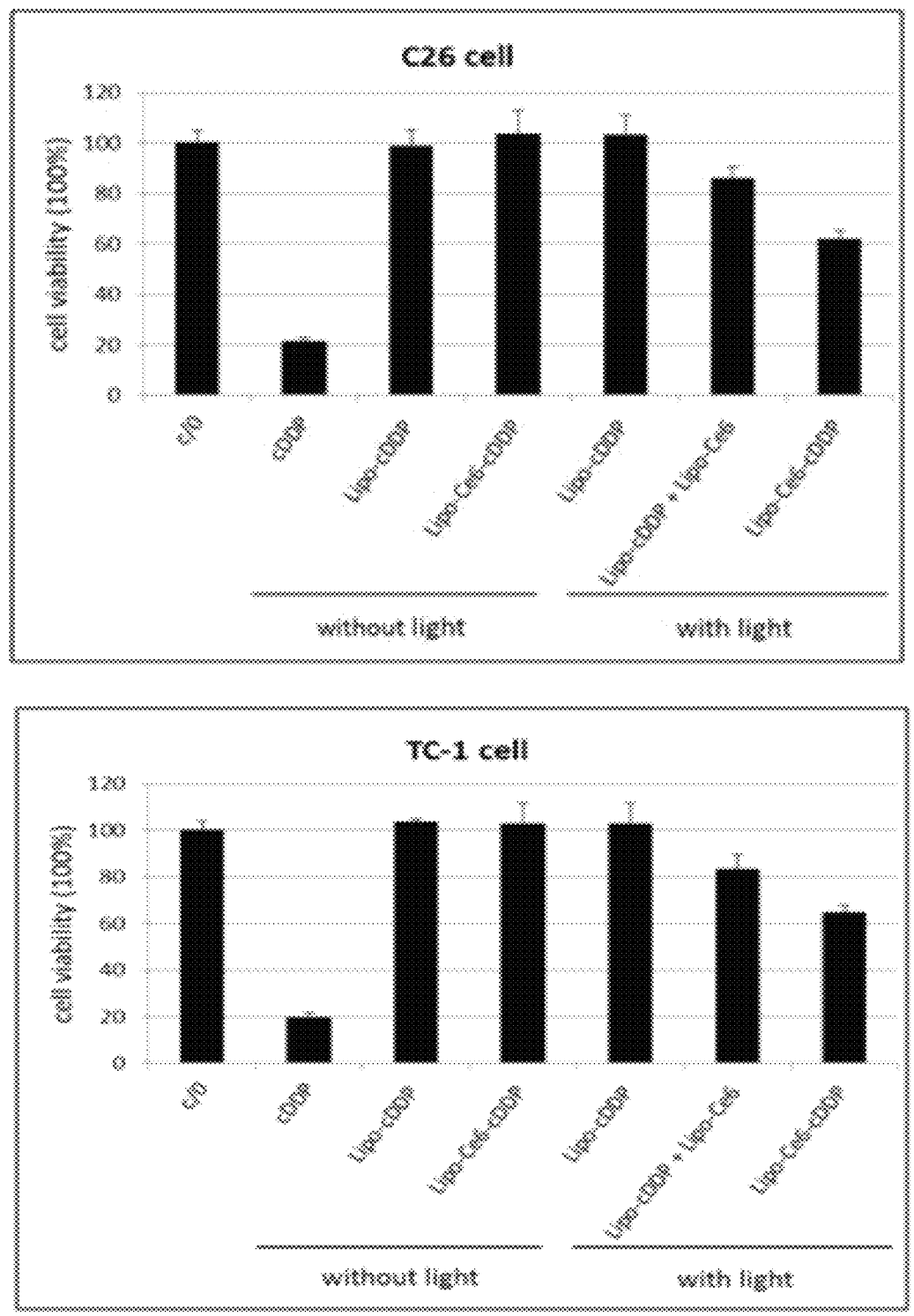
FIG. 8 shows that cell toxicity caused by Lipo-Ce6-cDDP was higher than that caused by Lipo-Ce6 and Lipo-cDDP in both C26 colon cell line and TC-1 cell line.

In the cytotoxicity assay, PDT was performed in C26 colon cell line and TC-1 cell line. As shown in FIG. 8, after PDT, cell toxicity caused by Lipo-Ce6-cDDP was higher than that caused by Lipo-Ce6 and Lipo-cDDP in both C26 colon cell line and TC-1 cell line.

Figure 9:
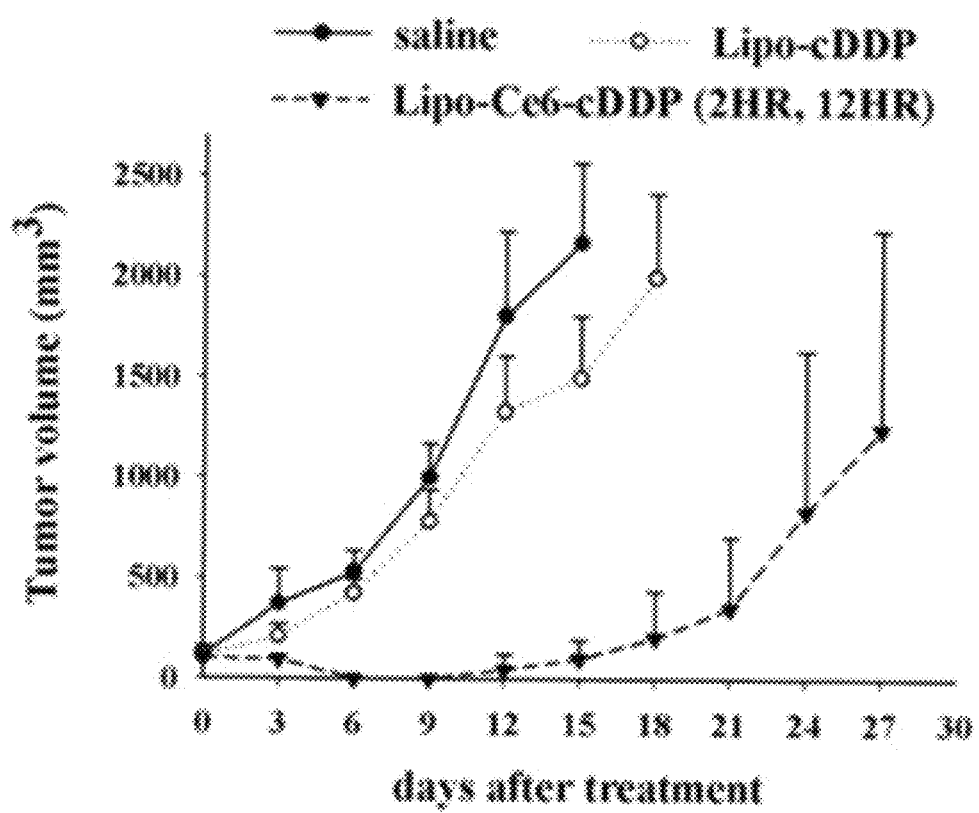
FIG. 9 shows in vivo PDT of Lipo-Ce6-cDDP. Single dose of dual-effect liposome (Ce6: 1.75 mg/kg; cDDP: 2.53 mg/kg) was administrated into BALB/cByJ mouse inoculated with at C26 mouse colon cancer cells through tail vein injection. Light irradiation (100 J/cm$^2$) was applied onto the tumor at different time post drug administration. (A) tumor size; (B) Survival rate (N=3). Tumors were measured and animal survival were monitored every three day until day 24 or tumor volume ≥2500 mm$^3$.
Figure 9:
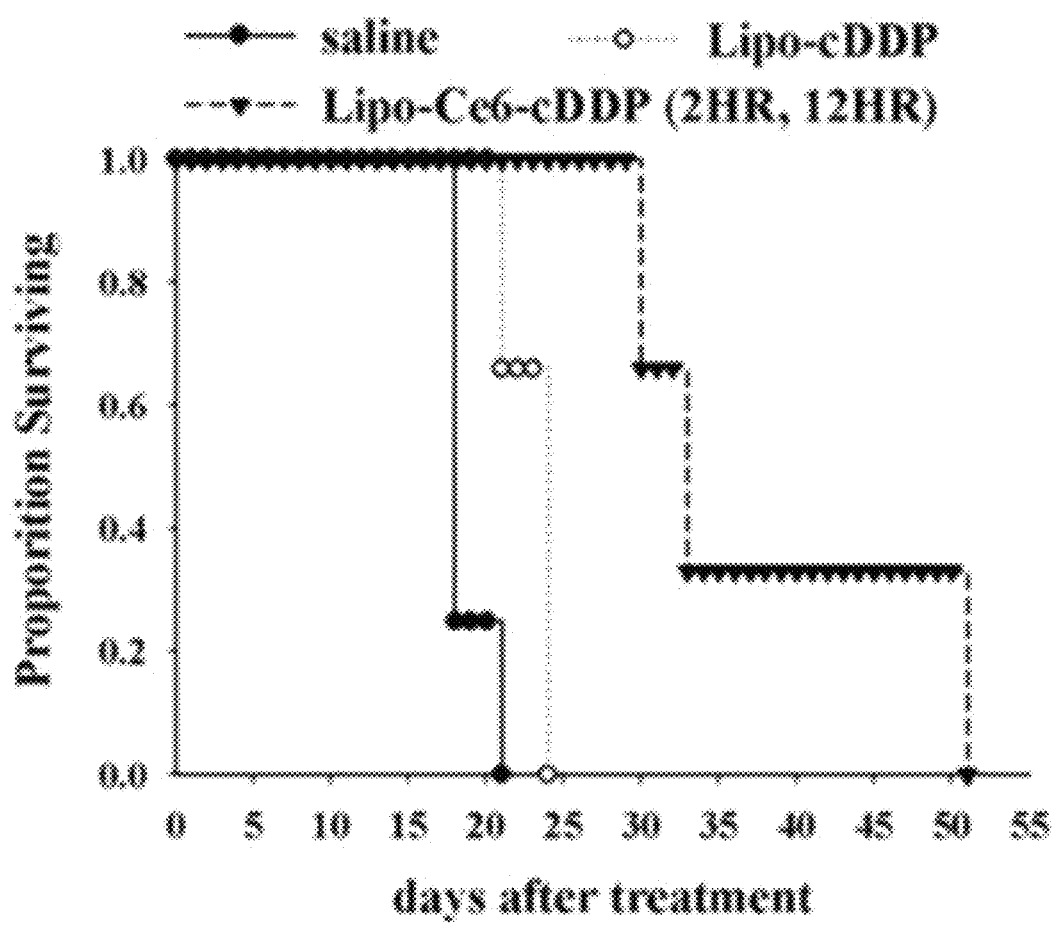
Figure 10:
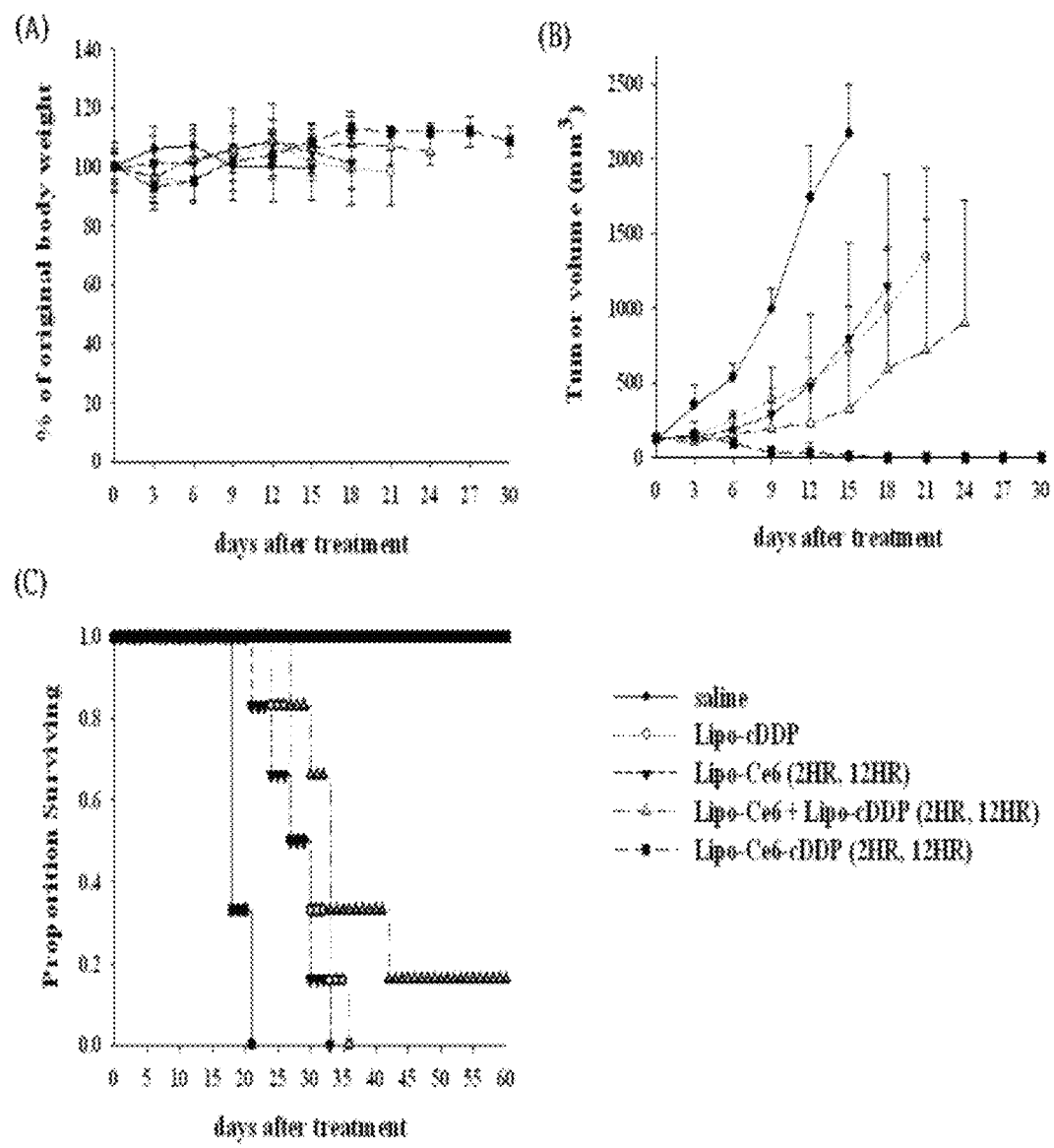
FIG. 10 shows in vivo PDT of Lipo-Ce6-cDDP. Single dose of dual-effect liposome (Ce6: 1.75 mg/kg; cDDP: 3.73 mg/kg) was administrated into BALB/cByJ mouse inoculated with at C26 mouse colon cancer cells through tail vein injection. Light irradiation (100 J/cm$^2$) was applied onto the tumor at different time post drug administration. (A) body weight; (B) tumor size; (C) Survival rate (N=6). Tumors were measured and animal survival was monitored.

Example 4 In Vivo Photodynamic Therapy Assay for Lipo-Ce6-cDDP and Lipo-Npe6-Dox The photodynamic therapy assay for Lipo-Ce6-cDDP and Lipo-Npe6-Dox was performed according to the procedures mentioned in Example 2. As shown in FIG. 9, Lipo-Ce6-cDDP with 1.75 mg/kg Ce6 and 2.53 mg/kg cDDP can effectively delay tumor growth after administering single dose of Lipo-Ce6-cDDP to BALB/cByJ mouse inoculated with C26 mouse colon cancer cells through tail vein injection and applying one-time light irradiation (100 J/cm$^2$) onto the tumor post administration of Lipo-Ce6-cDDP. Tumors were measured and animal survival were monitored every 3 days until day 24 or tumor volume ≥2500 mm$^3$. FIG. 10 shows that administration of Lipo-Ce6-cDDP with 1.75 mg/kg Ce6 and 3.73 mg/kg cDDP and application of two-times light irradiation (100 J/cm$^2$) after 2 and 12 hours of administration can completely eradiate tumors in BALB/cByJ mouse.

Figure 11:
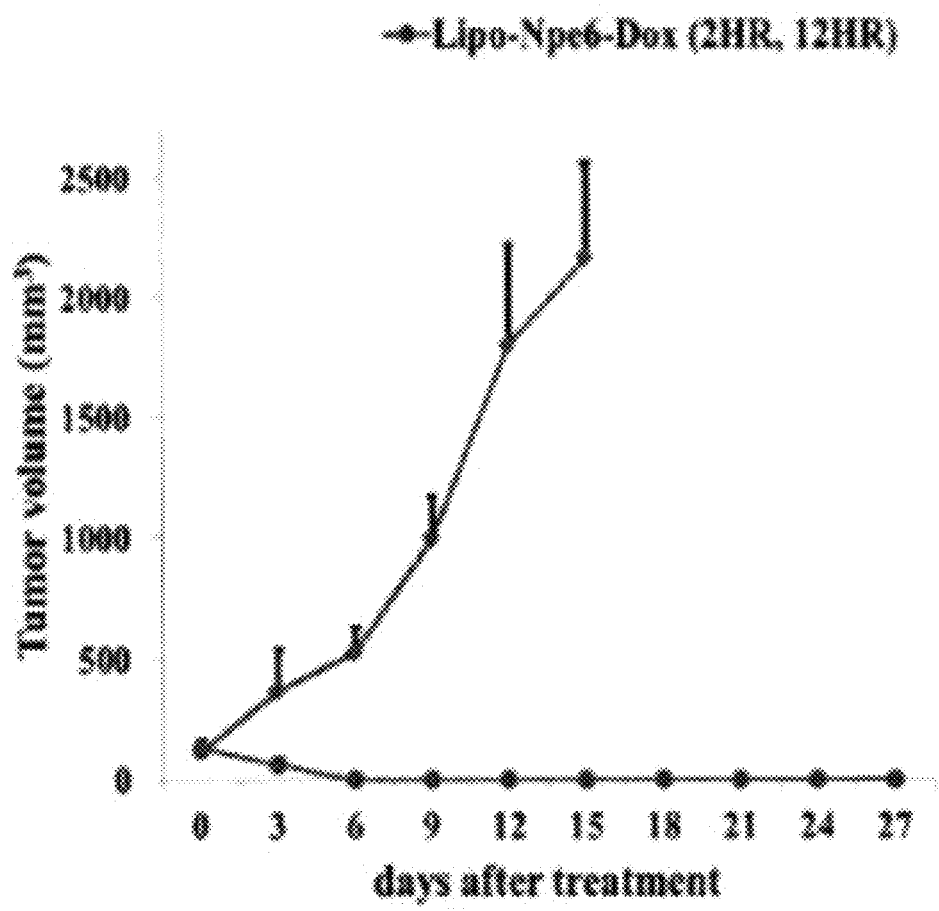
FIG. 11 shows that administration of Lipo-Npe6-Dox with 1.75 mg/kg Npe6 and 13.28 mg/kg Dox and application of two-times light irradiation (100 J/cm$^2$) after 2 and 12 hours of administration can significantly inhibit tumors with 100 mm$^3$ volume in BALB/cByJ mouse.

FIG. 11 shows that administration of Lipo-Npe6-Dox with 1.75 mg/kg Npe6 and 13.28 mg/kg Dox and application of two-times light irradiation (100 J/cm$^2$) after 2 and 12 hours of administration can significantly inhibit tumors in BALB/cByJ mouse.

Figure 12:
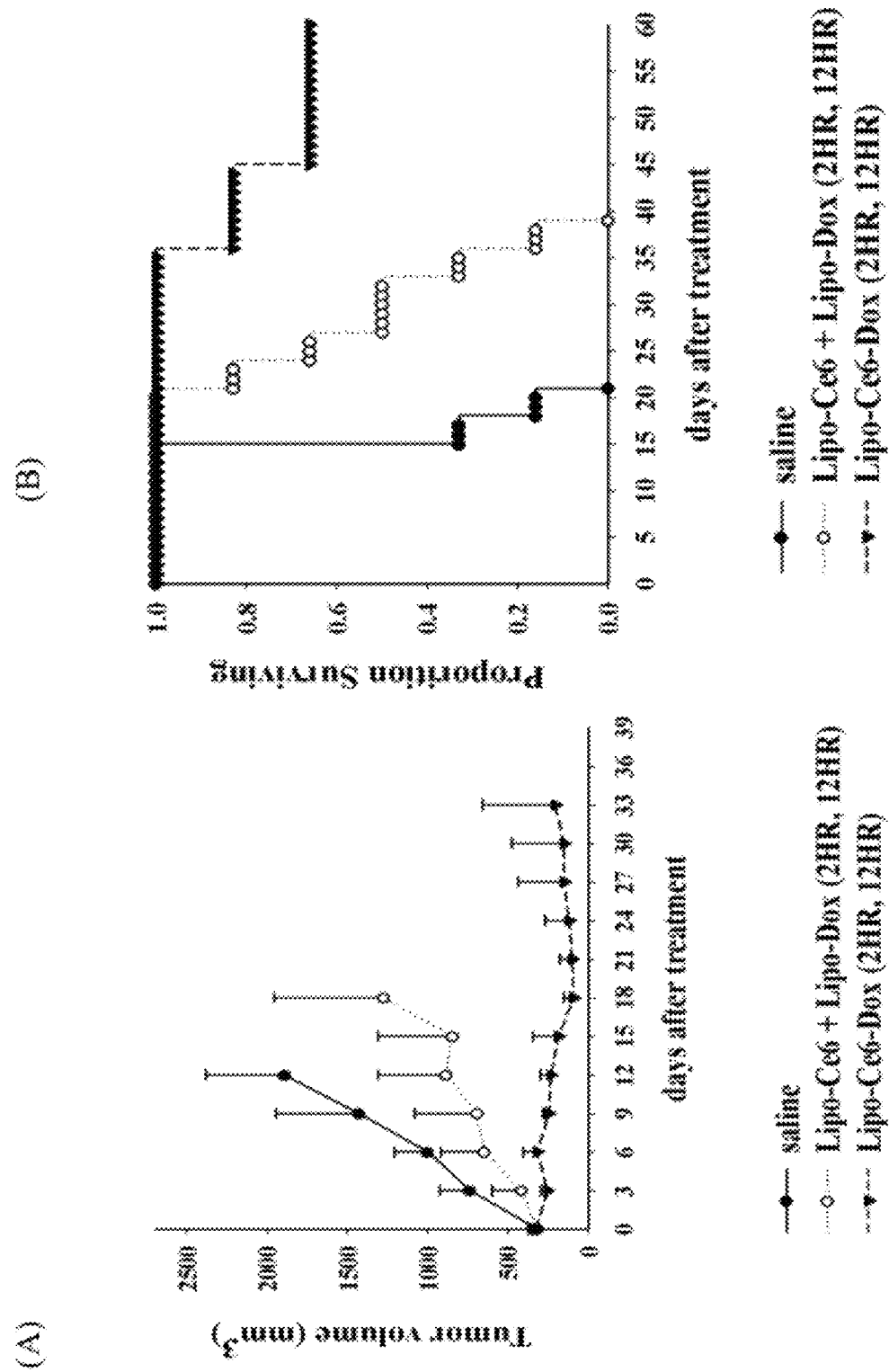
FIG. 12 shows that administration of Lipo-Ce6-Dox with 1.75 mg/kg Ce6 and 8.46 mg/kg Dox and application of two-times light irradiation (100 J/cm$^2$) after 2 and 12 hours of administration can significantly inhibit tumors with 300 mm$^3$ volume in BALB/cByJ mouse. (A) tumor size. (B) Survival rate (N=10).
Figure 13:
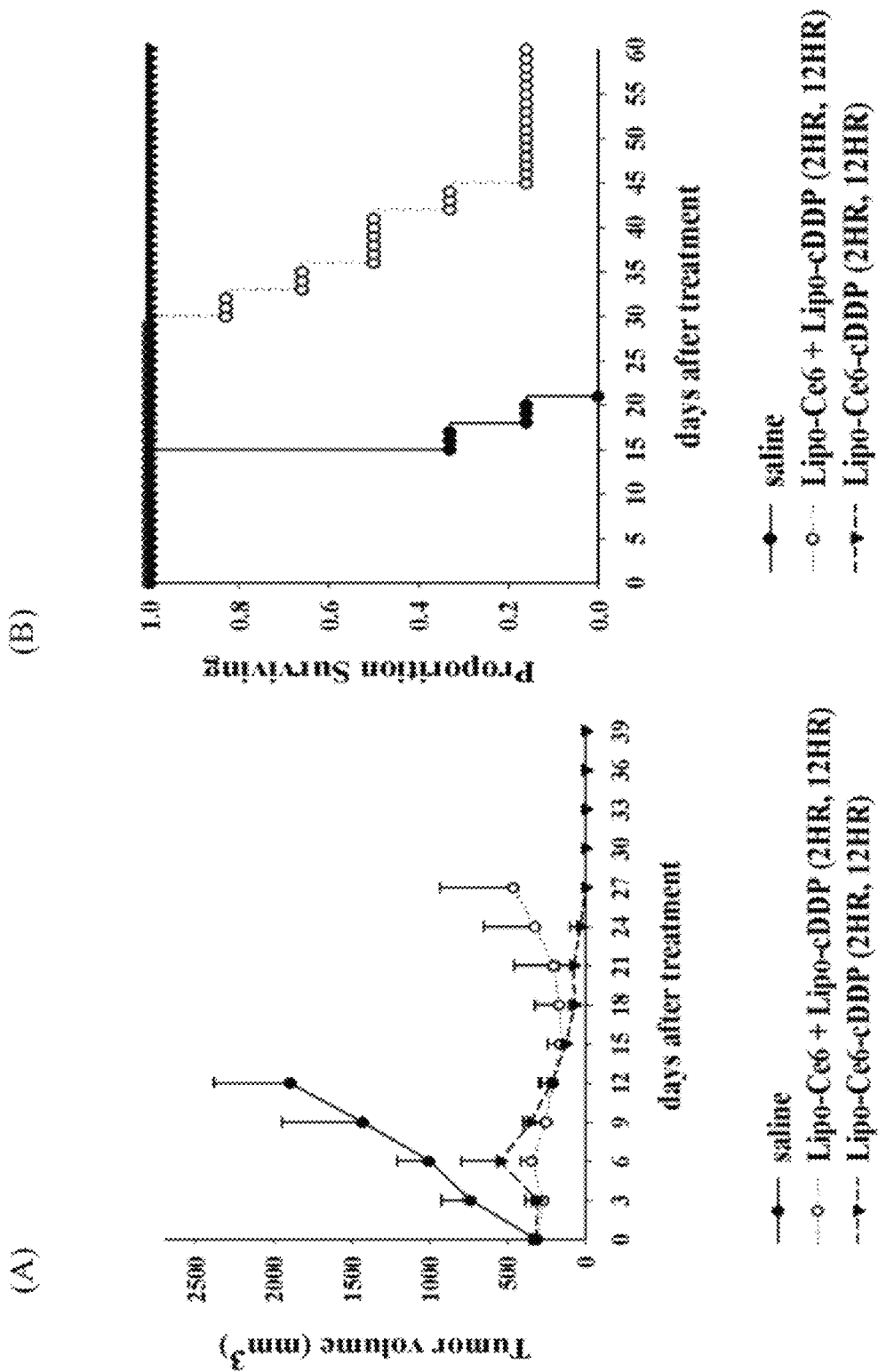
FIG. 13 shows that administration of Lipo-Ce6-Dox with 1.75 mg/kg Ce6 and 3.87 mg/kg cDDP and application of two-times light irradiation (100 J/cm$^2$) after 2 and 12 hours of administration can significantly inhibit tumors with 300 mm$^3$ volume in BALB/cByJ mouse. (A) tumor size. (B) Survival rate (N=10).
Figure 14:
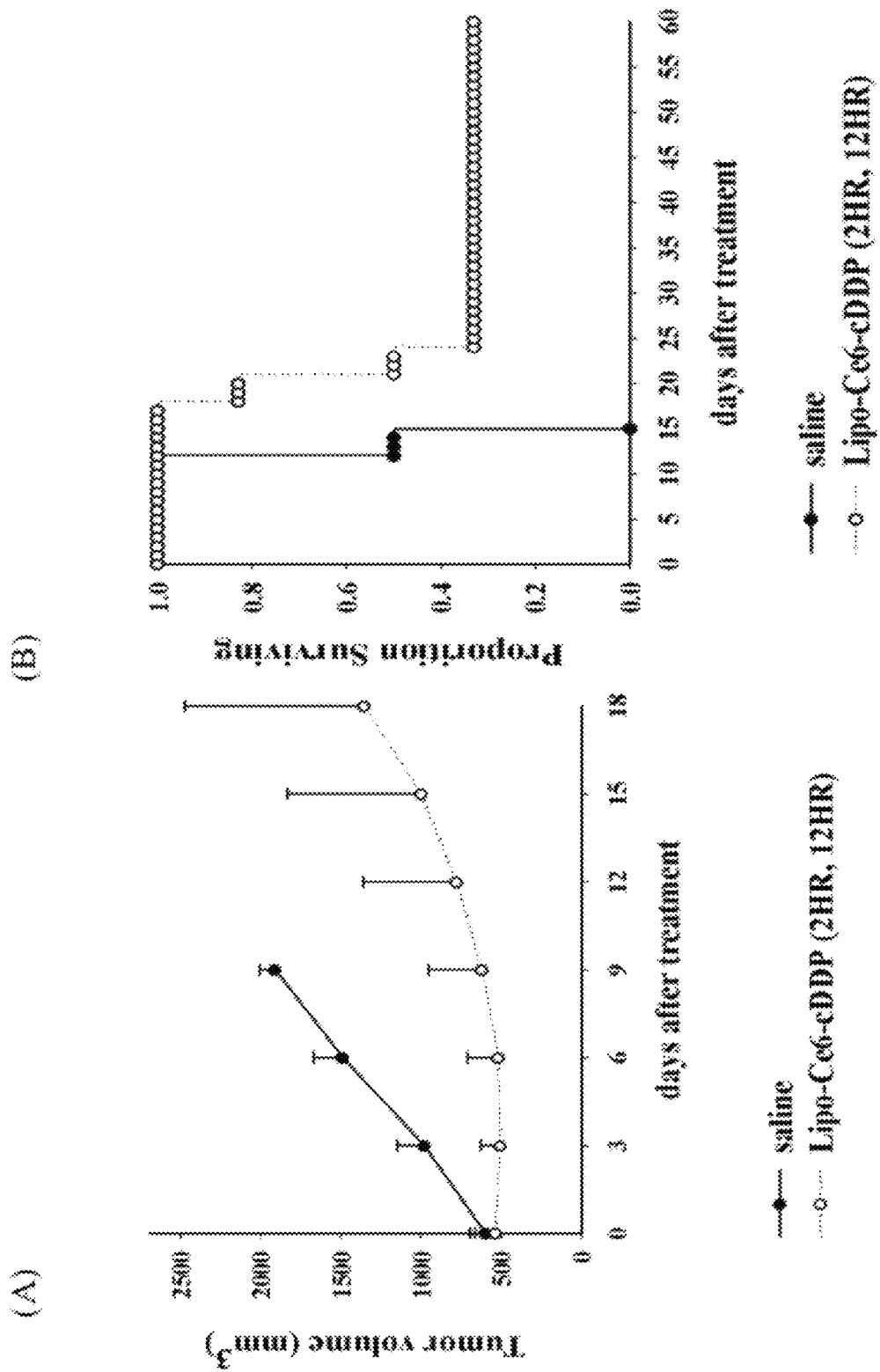
FIG. 14 shows that administration of Lipo-Ce6-Dox with 1.75 mg/kg Ce6 and 3.79 mg/kg cDDP and application of two-times light irradiation (100 J/cm$^2$) after 2 and 12 hours of administration can significantly inhibit tumors with 500 mm$^3$ volume in BALB/cByJ mouse. (A) tumor size. (B) Survival rate (N=10).

The photodynamic therapeutic regimen mentioned in Example 2 was used except that the tumor volumes are 300 and 500 mm$^3$, respectively, and the agent is Lipo-Ce6-Dox (1.75 mg/kg for Ce6 and 8.46 mg/kg for Dox and 1.75 mg/kg for Ce6 and 3.87 mg/kg for cDDP for tumor volume 300 mm$^3$) and Lipo-Ce6-cDDP (1.75 mg/kg for Ce6 and 3.79 mg/kg for cDDP for tumor volume 500 mm$^3$). It was surprisingly found that the tumors even with the volume of 500 mm$^3$ can be completely eliminated after three days of administering single dose of the above-mentioned agents. For the tumor volume with 300 mm$^3$ and 500 mm$^3$, as shown in FIGS. 12 and 13 (tumor volume with 300 mm$^3$) and FIG. 14 (tumor volume with 500 mm$^3$), Lipo-Ce6-Dox and Lipo-Ce6-cDDP can effectively cause tumor-free or delay tumor growth after administering single dose of Lipo-Ce6-Dox and Lipo-Ce6-cDDP to BALB/cByJ mouse inoculated with C26 mouse colon cancer cells through tail vein injection and applying one-time light irradiation (100 J/cm$^2$) onto the tumor post administration of Lipo-Ce6-Dox and Lipo-Ce6-cDDP. Tumors were measured and animal survival were monitored every 3 days until day 24 or tumor volume ≥2500 mm$^3$.

What is claimed is:

1. A method for treating a tumor in a subject, comprising (a) administering a therapeutically effective dose of liposome encapsulating a photosensitizer and an anti-tumor drug to a subject, wherein the liposome comprises a lipid bilayer comprising phospholipids and an aqueous interior, (b) performing a first irradiation to the tumor tissues at the time the liposome reaches the tumors, (c) performing a second irradiation to the tumor tissues at the time the anti-tumor drug released from the liposome accumulates at the tumor tissues to a maximum amount, and optionally (d) performing third or more irradiations to the tumor tissues; wherein the photosensitizer is 2-[7S8S)-3Carboxy-7-(2-carboxyethyl)-13-ethenyl-18-ethyl-7,8-dihydro-2,8,12,17-tetramethyl-21H,23H-porphin-5-yl]acetic acid (chlorin e6; Ce6) and the anti-tumor drug is cis-platin, wherein Ce6 is encapsulated within the lipid bilayer and cis-platin is encapsulated within the aqueous interior, and wherein the tumor is colon and rectal cancer, lung cancer, cervical cancer, oral cancer or malignant peripheral nerve sheath tumor.

2. The method of claim 1, wherein the administration is rectal, nasal, vaginal parenteral or topical.

3. The method of claim 1, wherein the administration is parenteral such as intravenous, subcutaneous, intramuscular, intradermal and intraperitoneal.

4. The method of claim 1, wherein the administration is intravenous.

5. The method of claim 1, wherein the tumor is sarcoma.

6. The method of claim 1, wherein the lung cancer is small cell lung cancer or non-small cell lung cancer.

* * * * *